(12) United States Patent
Thorup et al.

(10) Patent No.: US 7,915,504 B2
(45) Date of Patent: Mar. 29, 2011

(54) **FLOWER PIGMENTATION IN TETRAPLOID *LOBULARIA***

(75) Inventors: Troy Thorup, Arroyo Grande, CA (US); Tau-San Chou, Batavia, IL (US)

(73) Assignee: Ball Horticultural Company, West Chicago, IL (US)

( * ) Notice: Subject to any disclaimer, the term of this patent is extended or adjusted under 35 U.S.C. 154(b) by 272 days.

(21) Appl. No.: 12/124,576

(22) Filed: May 21, 2008

(65) Prior Publication Data

US 2009/0113568 A1    Apr. 30, 2009

Related U.S. Application Data

(63) Continuation-in-part of application No. 11/927,345, filed on Oct. 29, 2007, now abandoned.

(51) Int. Cl.
*A01H 1/00* (2006.01)
*A01H 4/00* (2006.01)
*A01H 5/00* (2006.01)
*A01H 5/10* (2006.01)

(52) U.S. Cl. .................... 800/323; 435/410; 800/260

(58) Field of Classification Search .................. None
See application file for complete search history.

(56) References Cited

OTHER PUBLICATIONS

Bali and Tandon 1959, Genetica XXX: 129-139.*
Tatsuzawa et al 2006, Phytochemistry 67: 1287-1295.*
Takamura et al 1996, Scientia Horticulturae 65: 305-312.*
Tatsuzawa et al Mar. 2007, Heterocycles 71(5): 1117-1125.*
Takamura, T., Sugimura, T., Tanaka, M. and Kage, T. 1998. Breeding of the Tetraploid Yellow-Flowered Cyclamen With "Eye". Acta Hort. (ISHS) 454:119-126 (Abstract Only).*
John M. Poehlman et al., 1995. Breeding Field Crops, Fourth Edition. Iowa State University Press / Ames. pp. 172-175.
PanAmerican/Ball Horticultural Grower Facts Sheet for Snow Crystals Alyssum. 2005.
U.S. Appl. No. 11/927,345, filed Apr. 30, 2009, Troy Thorup. et al., Office Action dated Apr. 19, 2010.
Dermen, Haig, "Colchicine Polyploidy and Technique," The Botanical Review, Nov. 1940, 6 (11): pp. 599-635.
Ancev, Minco, "Polyploidy and hybridization in Bulgarian Brassicaceae: distribution and evolutionary role," Phytologia Balcanica, Dec. 1, 2006, 12 (3): pp. 357-366.
Database Biosis [Online] Biosciences Information Service, 1987, "Cytotaxonomic Analysis of Representatives of the Section Odontarrhena C. A. Mey. Koch of the Genus *Alyssum* L. From the Flora of the Ukrainian SSR USSR"; Ukrayins'Kyi Botanichnyi Zhurnal, 44 (3): pp. 19-23.
U.S. Appl. No. 11/927,345, filed Apr. 30, 2009, Thorup, Troy.
U.S. Appl. No. 11/927,345, filed Apr. 30, 2009, Thorup, Troy, Office Action dated Apr. 16, 2010.
EP 08252978.5, May 6, 2009, Ball Horticultural Co., Corresponding European Application.
EP 08252978.5, May 6, 2009, Ball Horticultural Co., Extended Search Report dated Feb. 17, 2009.
EP 08252978.5, May 6, 2009, Ball Horticultural Co., Examination Report dated Aug. 7, 2009.
EP 08252978.5, May 6, 2009, Ball Horticultural Co., Response to Examination Report of Aug. 7, 2009 dated Feb. 11, 2010.
EU CPVR 2009/1010, Oct. 15, 2009, Ball Horticultural Co., Corresponding European Application.

* cited by examiner

*Primary Examiner* — David H Kruse
(74) *Attorney, Agent, or Firm* — Jondle & Associates, P.C.

(57) ABSTRACT

The present invention relates to novel tetraploid *Lobularia maritima* plants having pigmented flower petals. The present invention also relates to methods for creating novel tetraploid *Lobularia maritima* plants having pigmented flower petals.

15 Claims, No Drawings

FLOWER PIGMENTATION IN TETRAPLOID *LOBULARIA*

CROSS REFERENCE

This application is a continuation-in-part of U.S. application Ser. No. 11/927,345 filed on Oct. 29, 2007 which is hereby incorporated by reference.

TECHNICAL FIELD

The present invention relates to novel tetraploid *Lobularia maritima* plants having pigmented flower petals. The present invention also relates to methods for creating novel tetraploid *Lobularia maritima* plants having pigmented flower petals. All publications cited in this application are herein incorporated by reference.

BACKGROUND OF THE INVENTION

*Lobularia maritima*, alternately known as *Alyssum maritimum*, is native to Southern Europe and naturalized to the acid, sandy soils of the Western European coastal regions. In full bloom it emits a sweet aroma as expressed in its common name, sweet alyssum. Sweet alyssum is typically grown as an annual bedding plant for edging and ground cover purposes. It is multi-branched, widely spreading on the ground and reaches heights up to 30 cm. The leaves are green, narrow and linear. Flowers are dense, four-petalled, compact, terminal racemes. The flowers last over a long season and vary in size and color. Currently marketed series, such as Easter Bonnet, are diploid with flower colors that include white, apricot, pink, rose, lavender and violet. A karyological study identified 2n=24 for *Lobularia maritima*. [See Augustin, M., *Biologia* 48(4): 441-445 (1993).]

With any successful breeding program, there are numerous steps in the development of novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. For the horticultural industry, these important traits can include novel colors, resistance to diseases and insects, tolerance to drought and heat, or superior garden performance.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits can be used as parents to produce new populations for further selection.

These processes, which lead to the final step of marketing and distribution, require several from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents that possess favorable, complementary traits are crossed to produce an $F_1$ An $F_2$ population is produced by selfing one or several $F_1$. Selection of the best individuals can begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

The present invention relates to ploidy changes enabling introgression of flower pigmentation into tetraploid *Lobularia maritima*. Presently, the best garden performing *Lobularia maritima* is a white cultivar, the tetraploid Snow Crystals. The plants of the present invention will provide of novel, desirable and superior garden performing tetraploid *Lobularia maritima* with a range of flower colors.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above-described problems have been reduced or eliminated, while other embodiments are directed to other improvements.

This invention relates to novel *Lobularia maritima* plants having pigmented flower petals. These plants having pigmented *Lobularia maritima* flower petals were developed through unique tetraploid crosses.

This invention also relates to parts of tetraploid *Lobularia maritima* plants of the present invention and tissue cultures thereof. It further relates to tetraploid *Lobularia maritima* cultivars and hybrids having pigmented flower petals.

In addition, the present invention also relates to methods for creating novel tetraploid *Lobularia* varieties having pigmented flower petals using tetraploid *Lobularia maritima* having pigmented flower petals in breeding as either a female or male parent. The present invention also relates to an $F_1$ hybrid or a later generation *Lobularia maritima* plant grown from the *Lobularia maritima* seed produced by the aforementioned methods.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Allele. An allele is any of one or more alternative forms of a gene, all of which relate to one trait or characteristic. In a diploid cell or organism, the two alleles of a given gene occupy corresponding loci on a pair of homologous chromosomes.

Aglycon (Alglycone). Aglycon is the non-sugar compound remaining after replacement of the glycosyl group from a glycoside by a hydrogen atom.

Anthocyanidin. Anthocyanidin is an extended conjugation made up of the aglycon of the glycoside anthocyanins.

Anthocyanin. Anthocyanins are a class of flavonoids based on the cyanidin structure, differing in the presence or absence of hydroxyl groups by methylation or glycosylation, forming colored pigments. They are glycosylated versions of cyanidin, pelargonidin or delphinidin. The conjugated bonds result in blue, red, and purple colors in flowers of plants; for example, Anthocyanin (Glycoside)=Anthocyanidin (Aglycon)+Sugar (Glycone).

Backcrossing. Backcrossing is a process in which a breeder repeatedly crosses hybrid progeny back to one of the parents, for example, a first generation hybrid $F_1$ with one of the parental genotypes of the $F_1$ hybrid.

Colchicine. Colchicine is a poisonous, pale-yellow alkaloid, $C_{22}H_{25}NO_6$, obtained from the autumn crocus and used in plant breeding to induce chromosome doubling.

Cyanidin. Cyanidin is the aglycon of cyaninin. In plants cyanidin is bound to a sugar molecule to form cyanidin-3-glucoside.

Diploid. A diploid is a cell or organism having a pair of each type of chromosome (homologous pair), so that the basic chromosome number is doubled.

Colchicine-induced polyploidization. Colchicine-induced polyploidization is a technique wherein colchicine is used to inhibit the assembly of tublin subunits into spindle fibers, such that no chromosome movement can occur and hence cells at the metaphase stage of mitosis accumulate resulting in a doubling of the chromosome number.

Essentially all the physiological and morphological characteristics. A plant having essentially all the physiological and morphological characteristics means a plant having the physiological and morphological characteristics of the recurrent parent, except for the characteristics derived from the converted trait.

Glycosylated. Glycosylated is the result of the addition of saccharides to proteins and lipids.

Haploid. A haploid is a cell or organism having a single set of un-paired chromosomes.

Homozygous. Homozygous is a cell or organism having one or more gene loci on homologous chromosomes.

Hybrid. Hybrid means any offspring of a cross between two genetically unlike individuals (Rieger R., A. Michaelis and M. M. Green, 1968, A Glossary of Genetics and Cytogenetics, Springer-Verlag, N.Y.).

Inbred. An inbred means a substantially homozygous individual plant.

Inbreeding. In plants, inbreeding is a process in which a breeder crosses closely related plants increasing a plant's homozygosity.

Open pollinated. A plant pollinated without human agency.

Pelargonidin. Pelargonidin is the aglycon of pelargoninin. In plants pelargonidin is bound to a sugar molecule to form pelargonidin-3-glucoside.

Plant part or part of a plant. A plant part or part of a plant can include, but is not limited to cuttings, cells, protoplasts, cell tissue cultures, callus (calli), cell clumps, embryos, stamens, pollen, anthers, pistils, ovules, flowers, seed, petals, leaves, stems, and roots.

Polyploid. A polyploid is a cell or organism having a chromosome number that is more than double the haploid number of chromosomes.

Tetraploid. A tetraploid is a cell or organism having a chromosome number that is four times the haploid number of chromosomes.

Tissue culture. A plant tissue culture indicates a composition comprising isolated cells of the same or a different type or a collection of such cells organized into parts of a plant.

DETAILED DESCRIPTION OF THE INVENTION

The present invention relates to tetraploid *Lobularia maritima* plants having pigmented flower petals. The anthocyanins impart a range of reddish purple to dark lavender colors to the tetraploid *Lobularia maritima* flower petals.

Additionally, the present invention relates to parts of the tetraploid *Lobularia maritima* plants having pigmented flower petals. A plant part or part of a plant can include, but is not limited to cuttings, cells, protoplasts, cell tissue cultures, callus (calli), cell clumps, embryos, stamens, pollen, anthers, pistils, ovules, flowers, seed, petals, leaves, stems, and roots. More specifically the present invention relates to pollen, ovules, and cuttings of the tetraploid *Lobularia maritima* plants having pigmented flower petals.

The present invention also relates to a tissue culture comprising regenerable cells of the tetraploid *Lobularia maritima* plants of the present invention. The tissue culture will preferably be capable of regenerating plants having the physiological and morphological characteristics of the described tetraploid *Lobularia maritima* plants, and of regenerating plants having substantially the same genotype as the described tetraploid *Lobularia maritima* plants. Preferably, the regenerable cells in such tissue cultures can be leaf, pollen, embryo, cotyledon, hypocotyl, meristematic cell, root, root tip, pistil, anther, flower, stem, ovule, petiole and the like. In addition, the present invention provides tetraploid *Lobularia maritima* plants regenerated from the tissue cultures of the invention. Means for preparing and maintaining plant tissue culture are well known in the art. *Lobularia* is a member of the Cruciferae family and well-known to be amenable to tissue culture techniques. [See *Handbook of Plant Cell Culture* Vol. 3, Ammirato, P. V. et. al. ed., Macmillan, New York (1983) 227-246.]

The pigment in the petals of the tetraploid *Lobularia maritima* plants of the present invention is at least one anthocyanin and can be the glycosylated derivatives of cyanidin, or pelargonidin, or a combination thereof. Specifically, the present invention encompasses an anthocyanin content when assayed after hydrolysis, as aglycons, having at least about 0.05, 0.07, 0.10, 0.13, 0.15, 0.18, 0.20, 0.25, 0.28, 0.30, 0.34, 0.37, 0.41, 0.43, 0.47, 0.48, 0.52, 0.58, 0.66, 0.72, 0.81, 0.86, 0.94, 1.06, 1.08, 1.15, 1.20, 1.25, 1.33, 1.46, 1.57, 1.68, 1.77, 1.82, 1.94, 2.07, 2.15, 1.22, 2.34, 2.45, 2.58, 2.61, 2.73, 2.84, 2.97, 3.02, 3.13, 3.24, 3.36, 3.49, 3.52, 3.61, 3.78, 3.85, 3.99, 4.07, 4.14, 4.23, 4.34, 4.46, 4.58, 4.67, 4.72, 4.83, 4.91, 5.02, 5.11, 5.24, 5.36, 5.48, 5.59, 5.67, 5.89, 5.92, 6.05, 6.16, 6.28, 6.31, 6.43, 6.52, 6.67, 6.74, 6.85, 6.92, 7.01, 7.11, 7.23, 7.32, 7.46, 7.52, 7.68, 7.71, 7.88, 7.95, 8.00, 8.11, 8.21, 8.34, 8.46, 8.55, 8.63, 8.78, 8.82, 8.95, 9.01, 9.17, 9.28, 9.33, 9.46, 9.52, 9.68, 9.71, 9.83, 9.99, 10.02, 1.13, 10.25, 10.34, 10.41, 10.52, 10.63, 10.78, 10.85, 10.96, 11.00, 11.10, 11.20, 11.34, 11.44, 11.54, 11.64, 11.79, 11.87, 11.92, 12.06, 12.12, 12.23, 12.31, 12.41, 12.58, 12.64, 12.74, 12.83, 12.92, 13.06, 13.17, 13.27, 13.39, 13.41, 13.56, 13.68, 13.72, 13.88, 13.91, 14.07, 14.15, 14.25, 14.34, 14.45, 14.69, 14.70, 14.84, 14.95, 15.03, 15.13, 15.25, 15.36, 15.41, 15.24, 15.56, 15.68, 15.74, 15.81, 15.92, 16.01, 16.15, 16.25, 16.34, 16.44, 16.52, 16.68, 16.71, 16.82, 16.99, 17.01, 17.13, 17.26, 17.34, 17.55, 17.60 and higher, mg/g petal dry weight when assayed after hydrolysis as aglycons. We have found that the petal anthocyanin concentrations have increased with breeding and selection, and with continued breeding, higher petal anthocyanin concentrations are found.

In addition, the present invention relates to a method of producing a first generation ($F_1$) hybrid *Lobularia maritima* plant. The method involves crossing a first parent tetraploid *Lobularia maritima* plant with a second parent tetraploid *Lobularia maritima* plant and harvesting the resultant first generation ($F_1$) hybrid tetraploid *Lobularia maritima* seed, and selecting a hybrid plant. Either or both of the first parent or second parent tetraploid *Lobularia maritima* plants can be a tetraploid *Lobularia maritima* plant having pigmented flower petals. Additionally, the present invention relates to a first generation ($F_1$) hybrid tetraploid *Lobularia maritima* plant or a part thereof produced by the method described above. The flower pigmentation does not limit seed yield. Seed production is indistinguishable from standard *Lobularia maritima* breeding. Thousands of seeds have been developed using *Lobularia maritima* plants having pigmented flower petals.

Further, the present invention relates to a method of producing an inbred *Lobularia maritima* plant. The method involves self- or sib-pollinating a tetraploid *Lobularia maritima* plant having pigmented flower petals, recovering the resulting seed, planting the resulting seed and growing into plants, and selecting one or more progeny plants; self- or sib-pollinating the selected plant, recovering the resulting seed, planting the resulting seed and growing into plants, and selecting a plant; and repeating the previous step until an $F_4$ or later generation inbred is selected.

The present invention also relates to an inbred tetraploid *Lobularia maritima* plant or plant part thereof produced by the method described above. Furthermore, the present invention relates to a hybrid produced from a cross using an inbred tetraploid *Lobularia maritima* plant produced by the method described above.

Finally, the present invention relates to viable *Lobularia maritima* seeds and plants and succeeding generations thereof which are grown from seeds of the present invention.

Using the methods described herein, it is expected that additional tetraploid *Lobularia maritima* plants having pigmented flower petals can be created. It is further expected that any *Lobularia maritima* tetraploid plant having pigmented flower petals can be crossed with any other tetraploid *Lobularia maritima*.

Tetraploids can occur spontaneously in nature or be induced using spindle fiber inhibitors such as colchicine. The technique of colchicine-induced polyploidization has been used since the 1930's. Colchicine inhibits the assembly of tublin subunits into spindle fibers, such that no chromosome movement can occur and hence cells at the metaphase stage of mitosis accumulate. When the chromatids separate, but are not divided into separate cells by the spindle, the chromosome number is doubled creating an autopolyploid. When creating a polyploid for breeding purposes the layer of the apical meristem that gives rise to the gametophytic tissue needs to be doubled. To optimize the probability of successful doubling, a high number of small, actively growing meristems should be treated. Usually colchicine is used at a concentration of 0.1 to 0.9% depending on the tissue and the species. Methods for treating seeds with colchicine or other spindle fiber inhibitors are well-known in the art.

Ploidy changes affect crossability, fertility, cell size and heterozygosity, factors offering potential benefits as well as limitations in plant breeding. Ploidy manipulation has been used for the introgression of germplasm between taxa of different ploidy. For example, to overcome $F_1$ sterility of interspecific *Lilium* hybrids, colchicine was used for the induction of tetraploids. Interspecific crosses at the tetraploid level between complex hybrids of four *Lilium* species were made. [See Tuyl, J. M. et al., *Acta Horticulturae* 414: 35-45 (1996).] Tetraploid plants of *Buddleja globosa*, which is naturally diploid, were produced using colchicine treatment and have been crossed with natural tetraploid *Buddleja davidii* to introgress yellow flower color into *Buddleja davidii*. [See Rose, J. B. et al., *Acta Horticulturae* 560: 109-112 (2001).] All yellow-flowered *Cyclamen persicum* cultivars are diploid and do not have "eyes" on the petals. Using colchicine treatment, a tetraploid yellow flowered cyclamen was induced. After crossing with tetraploid "eyed" cultivars segregation was such that yellow-flowered "eyed" selections could not be maintained by seed. [See Takamura, T. et al., *Acta Horticulturae* 454: 119-126 (1998).]

The flower industry strives to develop new and different varieties of flowering plants. An effective way to create such novel varieties is through the manipulation of flower color. Flower color is predominantly due to two types of pigment: flavonoids and carotenoids. Flavonoids contribute to a range of colors from yellow to red to blue. Carotenoids impart a reddish-orange or yellow tinge and are commonly the only pigment in yellow or orange flowers. The flavonoid molecules which make the major contribution to flower color are the anthocyanins which are glycosylated derivatives of cyanidin, delphinidin, petunidin, peonidin, malvidin and pelargonidin, and are localised in the vacuole. The different anthocyanins can produce marked differences in color. Flower color is also influenced by co-pigmentation with colorless flavonoids, metal complexation, glycosylation, acylation, methylation and vacuolar pH. [See Forkman, G., *Plant Breeding* 106:1-26 (1991).]

The following examples are set forth as representations of specific and preferred embodiments of the present invention. These examples are not to be construed as limiting the scope of the invention in any manner. It should be understood that many variations and modifications can be made while remaining within the spirit and scope of the invention.

EXAMPLES

Example 1

Colchicine Treatment of *Lobularia maritima* Seed

The previously unknown tetraploid *Lobularia maritima* having pigmented flower petals were discovered as a result of breeding and research efforts which were conducted in West Chicago, Ill. and Santa Paula, Calif. In December 2000, seed from diploid *Lobularia maritima* cultivars Easter Bonnet Purple, White, Rose, Lavender, and Pink and Aphrodite Salmon and Cream were treated with colchicine. For this treatment, approximately 100 to 200 seeds of an individual variety were added to a 125 ml Erlenmeyer flask containing approximately 50 ml of sterile distilled water. Each flask was maintained on a rotary shaker at approximately 100 rpm until the majority of the seeds showed evidence of radical emergence, which was typically in four to seven days. At this stage of seed development, the water was decanted and replaced with approximately 50 ml of a 0.1% colchicine and 2% DMSO (dimethyl sulfoxide) solution (chemicals purchased from Sigma Chemical Co., St. Louis, Mo.). After 24 to 36 hours, the colchicine containing solution was decanted and replaced with sterile distilled water for a rinse treatment. The water was decanted and replaced every two hours for a total of five times. The final rinse was continued for an additional two to 14 hours. Seeds were removed from the flask and transferred to a Petri dish containing a layer of filter paper moistened with sterile distilled water. Plates were sealed with parafilm and shipped to the breeding facility at Santa Paula, Calif.

Example 2

Breeding of Tetraploid *Lobularia maritima* by Crossing Tetraploid-Induced Easter Bonnet Purple with Snow Crystals At the breeding facility, treated and untreated seeds were planted and grown to flowering. A cross was made using the colchicine-induced tetraploid Easter Bonnet Purple as the male parent and a selection from Snow Crystals (commercially available from PanAmerican Seed Co., West Chicago, Ill. 60185) as the female parent. The resulting $F_1$ seed was collected and germinated. From the flowering progeny, plants identified as (S.C.-1×CEBV-7)-1, (S.C.-1×CEBV-1)-1A, (S.C.-1×CEBV-1)-1B, (S.C.-2×CEBV-1)-1, (S.C.-1×CEBV-1)-2, were selected. The $F_1$ generation yielded plants with an intermediate plant vigor between standard diploid *Lobularia maritima* and Snow Crystals. Flower size was equal to or greater than that of Snow Crystals, and all flowers were white, with no evidence of pigmentation. Selfed seed was collected from the $F_1$ selections. $F_2$ selections were made based upon the presence of pigmentation in the flower petals. Pigmented flowers segregated at <1%. The selections were massed in groups of 4 to 6 based upon pedigree. $F_3$ selections were based upon presence of pigmentation in the flower. Plants were massed in groups of 4 to 6 based upon pedigree. All subsequent generations have followed this procedure until uniform inbreds were developed.

Selections with the deepest pigmentation have been backcrossed to Snow Crystals. Selections from these backcrosses follow the same procedures outlined above until inbred lines are developed.

Example 3

Breeding of Tetraploid *Lobularia maritima* by Crossing Tetraploid-Induced Easter Bonnet Pink with Snow Crystals At the breeding facility, treated and untreated seeds were planted and grown to flowering. A cross was made using the colchicine-induced tetraploid Easter Bonnet Pink as the male parent and a selection from Snow Crystals (commercially available from PanAmerican Seed Co., West Chicago, Ill. 60185) as the female parent. The resulting $F_1$ seed was collected and germinated. From the flowering progeny, plants identified as (S.C.-1×CEBP-1)-1, (S.C.-1×CEBP-3)-1, (S.C.-1×CEBP-3)-2, (S.C.-1×CEBP-3)-3, (S.C.-1×CEBP-3)-4, were selected. The $F_1$ generation yielded plants with an intermediate plant vigor between standard diploid *Lobularia maritima* and Snow Crystals. Flower size was equal to or greater than that of Snow Crystals, and all flowers were white, with no evidence of pigmentation. Selfed seed was collected from the $F_1$ selections. $F_2$ selections were made based upon the presence of pigmentation in the flower petals. Pigmented flowers segregated at <1%. The selections were massed in groups of 4 to 6 based upon pedigree. $F_3$ selections were based upon presence of pigmentation in the flower. Plants were massed in groups of 4 to 6 based upon pedigree. All subsequent generations have followed this procedure until uniform inbreds were developed.

Selections with the deepest pigmentation have been backcrossed to Snow Crystals. Selections from these backcrosses follow the same procedures outlined above until inbred lines are developed.

Example 4

Breeding of Tetraploid *Lobularia maritima* by Crossing Tetraploid-Induced Easter Bonnet Red with Snow Crystals At the breeding facility, treated and untreated seeds were planted and grown to flowering. A cross was made using the colchicine-induced tetraploid Easter Bonnet Red as the male parent and a selection from Snow Crystals (commercially available from PanAmerican Seed Co., West Chicago, Ill. 60185) as the female parent. The resulting $F_1$ seed was collected and germinated. From the flowering progeny, plants identified as (S.C.-1×CEBR-1)-1, (S.C.-2×CEBR-1)-1, (S.C.-2×CEBR-1)-2, were selected. The $F_1$ generation yielded plants with an intermediate plant vigor between standard diploid *Lobularia maritima* and Snow Crystals. Flower size was equal to or greater than that of Snow Crystals, and all flowers were white, with no evidence of pigmentation. Selfed seed was collected from the $F_1$ selections. $F_2$ selections were made based upon the presence of pigmentation in the flower petals. Pigmented flowers segregated at <1%. The selections were massed in groups of 4 to 6 based upon pedigree. $F_3$ selections were based upon presence of pigmentation in the flower. Plants were massed in groups of 4 to 6 based upon pedigree. All subsequent generations have followed this procedure until uniform inbreds were developed.

Selections with the deepest pigmentation have been backcrossed to Snow Crystals. Selections from these backcrosses follow the same procedures outlined above until inbred lines are developed.

Example 5

Breeding of Tetraploid *Lobularia maritima* by Crossing Tetraploid-Induced Aphrodite Apricot with Snow Crystals At the breeding facility, treated and untreated seeds were planted and grown to flowering. A cross was made using the colchicine-induced tetraploid Aphrodite Apricot as the male parent and a selection from Snow Crystals (commercially available from PanAmerican Seed Co., West Chicago, Ill. 60185) as the female parent. The resulting $F_1$ seed was collected and germinated. From the flowering progeny, plants identified as (S.C.-1×CEBAP-1)-1, (S.C.-1×CEBAP-1)-2, (S.C.-2×CEBAP-1)-1, (S.C.-2×CEBAP-1)-2, were selected. The $F_1$ generation yielded plants with an intermediate plant vigor between standard diploid *Lobularia maritima* and Snow Crystals. Flower size was equal to or greater than that of Snow Crystals, and all flowers were white, with no evidence of pigmentation. Selfed seed was collected from the $F_1$ selections. $F_2$ selections were made based upon the presence of pigmentation in the flower petals. Pigmented flowers segregated at <1%. The selections were massed in groups of 4 to 6 based upon pedigree. $F_3$ selections were based upon presence of pigmentation in the flower. Plants were massed in groups of 4 to 6 based upon pedigree. All subsequent generations have followed this procedure until uniform inbreds were developed.

Selections with the deepest pigmentation have been backcrossed to Snow Crystals. Selections from these backcrosses follow the same procedures outlined above until inbred lines are developed.

Example 6

Cytological Analysis of Tetraploid *Lobularia maritima*

To determine chromosome number, cytological analysis was conducted. Three selections of the present invention, 13311-10, 13330-5, and 13322-4 and four currently marketed *Lobularia maritima* varieties were analyzed. Currently marketed varieties included tetraploid Snow Crystals and diploid Easter Bonnet Lavender, Easter Bonnet Violet and Easter Bonnet White.

To identify flower petal pigmentation, colors were determined under natural daylight conditions using The R.H.S. Color Chart of The Royal Horticultural Society, London, England, 2001 edition. The data in column 2 of Table 1 shows that all RHS values for the tetraploid *Lobularia maritima* plants of the present invention are in the red purple to violet range.

Methods for determining chromosome numbers are well known in the art. [See Zhao and Davidson, *Caryologia* 37: 331-342 (1984), and Davidson et. al., *Can. J. Genet. Cytol* 25: 437-445 (1983).] Following well-known procedures, root samples from each plant were collected and pretreated at 4° C. for 24 hours for chromatin condensation and accumulation of mitotic index. The root samples were fixed in a 100% ethanol and glacial acetic acid fixative (3:1 v/v ratio). The root samples were then rinsed with water for approximately 10 minutes and then treated with 1N HCl for seven minutes. The root samples were stained with Feulgen solution for one hour prior to cytological analysis.

As shown in column 3 of Table 1, analysis confirmed that selections 13311-10, 13330-5 and 13322-4 of the present invention and Snow Crystals are tetraploid (4n=48). In addition, analysis confirmed that the marketed varieties Easter Bonnet Lavender, Easter Bonnet Violet and Easter Bonnet White are diploids (2n=24).

TABLE 1

Comparison of color values and chromosome number of *Lobularia maritima* selections

| Plant | Color (RHS Value) | Chromosome No. |
|---|---|---|
| 13330-5 | Closest to 83A | 48 |
| 13311-10 | 85B | 48 |
| 13322-4 | 72A | 48 |
| Snow Crystals | Purer white than 155D | 48 |
| Easter Bonnet Violet | 83A | 24 |
| Easter Bonnet Lavender | 85B | 24 |
| Easter Bonnet White | Purer white than 155D | 24 |

Table 2 compares the differences in flower diameter between the tetraploid *Lobularia* of the present invention with Snow Crystals and standard diploid *Lobularia*. The flower diameter was calculated as the average diameter of ten flowers of each variety. Plants were grown in 10 cm pots under standard greenhouse conditions. Column one shows the variety or selection identification, column two shows the color of the variety and column three shows the average flower diameter in millimeters. Data analysis using the Student t-Test indicates a significant difference at the $\alpha=0.05$ level between the diploid and tetraploid flowers in each color class. In addition, selection 13330-5 had significantly larger flowers than the tetraploid Snow Crystals.

TABLE 2

Comparison of flower diameter between the tetraploid *Lobularia* of the present invention, Snow Crystals and standard diploid *Lobularia*.

| Plant | Ploidy | Color | Flower Diameter (mm) |
|---|---|---|---|
| 13330-5 | Tetraploid | Violet | 7.0 |
| 13311-10 | Tetraploid | Lavender | 6.5 |
| Snow Crystals | Tetraploid | White | 6.1 |
| Easter Bonnet Violet | Diploid | Violet | 4.8 |

TABLE 2-continued

Comparison of flower diameter between the tetraploid Lobularia of the present invention, Snow Crystals and standard diploid Lobularia.

| Plant | Ploidy | Color | Flower Diameter (mm) |
|---|---|---|---|
| Easter Bonnet Lavender | Diploid | Lavender | 5.9 |
| Easter Bonnet White | Diploid | White | 5.0 |

Example 7

Anthocyanin Analysis of Tetraploid Lobularia maritima

Flower petals from three selections of the present invention, 13311-10, 13330-5, and 13322-4, and the variety Snow Crystals were analyzed for their anthocyanin content. Methods for anthocyanin analysis are well-known in the art. [See Zhang, Z., et al., *J. Agric. Food Chem.* 52: 688-691 (2004), and Kazuma, K., et al., *Phytochemistry* 62: 229-237 (2004).] The method used in this analysis included a comparison of HPLC profiles of the hydrolysates with anthocyanidin standards, with spectrophotometric quantification of anthocyanins as their aglycons.

Preparation of Tetraploid Lobularia maritima Anthocyanin Samples

For this analysis, petals from the flowers of each plant were collected, lyophilized, powdered and saved at −20° C. until analysis. For each plant sample, 10 mg of lyophilized and powdered material was placed into a 12 ml screw-capped test tube. The mixture was blended with 3 ml of 2N HCl. The test tube was heated at 100° C. for 60 minutes and then the solution was cooled to room temperature. To the hydrolysate, 3 ml water was added. The solution was transferred onto an equilibrated Waters SEP-PAK cartridge (12 CC, C18, 2 g). The cartridge was equilibrated by eluting with 5 ml of 0.01% HCl in methanol and then 0.01% HCl in water. The test tube mixture was washed with 2 ml of water and the solution was transferred to the cartridge. The cartridge was washed with another 4 ml of water. The cartridge was eluted with 5 ml of acetonitrile (AN) and 0.1% trifluoro acetic acid (TFA) in water mixture in a ratio of 40:60. The solution was filtered using a 0.45µ filter in preparation for HPLC analysis.

Preparation of Anthocyanin Standards

Procedures for preparing anthocyanin standards are well known in the art. [See Zhang, Z., et al., *J. Agric. Food Chem.*, 52: 688-691 (2004).] For this analysis, anthocyanin standards of delphinidin, cyanidin, petunidin, peonidin and malvidin were prepared from bilberry extract using approximately 1.5 grams, four capsules, of bilberry extract (obtained from NATURES RESOURCE, Mission Hills, Calif.). Five ml of 3N HCl was added to the bilberry extract contained in a 12 ml screw-cap test tube. The mixture was heated on a heating block for 1 hour at 100° C., and then diluted with 5 ml of water. The solution was transferred to an equilibrated Waters SEP-PAK cartridge (12 CC, C18, 2 g). For cartridge equilibration, 5 ml of 0.01% HCl in methanol was added to the cartridge. After the solution drained, 10 ml of 0.01% HCl was added. Following equilibration and transfer of the solution, the cartridge was washed with 10 ml of 0.01% HCl. The cartridge was eluted with 0.01% HCl in methanol until the anthocyanidins eluted. For spectrophotometric analysis, the amount of anthocyanidin was calculated from the absorbance at 535 nm. For HPLC use, a 500 µg aliquot of each anthocyanin was transferred into an amber vial. To prepare the standard solution, each 500 µg aliquot was dissolved in 2 ml 40% AN: 60% (0.1% TFA) to yield an anthocyanin concentration of 0.25 mg/ml.

To prepare the pelargonidin standard, 120 g of fresh strawberry fruit was transferred to an Erlenmeyer flask and blended. The fruit was stirred with 100 ml acetone with a magnetic stirrer for 30 minutes then filtered through glass wool. The procedure was repeated, extracts combined, and evaporated to dryness. After drying, 10 ml of 3N HCl was added into 300 mg of the extract. The mixture was heated on a block for 2 hours at 100° C. The solution was transferred to a column equilibrated as noted above. The column was washed with 30 ml of 0.01% HCl and eluted with 10 ml of 0.01% HCl in methanol. For spectrophotometric analysis, the amount of anthocyanidin was calculated from the absorbance at 535 nm. For HPLC use, aliquots of 0.1 µg/ml anthocyanin were transferred into amber vials. To prepare the standard pelargonidin solution for HPLC, 0.1 µg of anthocyanin was dissolved in 1 ml 40% AN: 60% (0.1% TFA).

HPLC Analysis of Anthocyanin Standards

For HPLC analysis, a ZORBAX SB-18, 4.6×150 mm, 3.5µ column was used. The solvents for the mobile phase were 0.2% TFA and 0.2% TFA in acetonitrile. Anthocyanins were separated using a gradient method. Initial gradient conditions were 85% of 0.2% TFA: 15% 0.2% TFA in acetonitrile. From 6 to 20 minutes, the mobile phase was changed from the initial conditions to 78% of 0.2% TFA:22% 0.2% TFA in acetonitrile, and from 20 to 35 minutes to 70% of 0.2% TFA:30% 0.2% TFA in acetonitrile. After 40 minutes, the mobile phase was returned to the initial conditions and the column equilibrated for an additional 10 minutes. The column temperature was maintained at 26° C. and the flow rate was 1.0 ml/minute. Injections were 10 µl. The peak responses were measured by absorbance at 520 nm.

UV/VIS Spectrum Analysis of Samples

To quantify the petal anthocyanin concentration, 1 ml of each sample was evaporated to dryness then reconstituted in 0.1% HCl in ethanol. Wavelengths were determined from the UV/VIS spectrum of the sample and were compared with values reported in the literature. [See Guisti, M. et. al., *J. Agric. Food Chem.* 47: 4631-4637 (1999).] Data shown in Table 3 identifies mean (average) anthocyanin quantities for the petal tissue of three selections of the present invention compared to undetectable presence of anthocyanin in the commercially available Snow Crystals petals. Anthocyanin levels as low as 0.05 mg/gram dry weight were detected for the tetraploid Lobularia of the present invention.

TABLE 3

Identification of anthocyanins in tetraploid Lobularia maritima petals

| Selection | Wavelength* | Dilution | Absorbance | Anthocyanin (mg/gm petal dry wt.) |
|---|---|---|---|---|
| 'Snow Crystals' | — | — | — | 0 |
| 13322-4 | 504.5 | 2 | 0.590 | 10.8[1] |
| 1331-10 | 547 | 1 | 0.752 | 3.7[2] |
| 13330-5 | 547 | 4 | 0.897 | 17.6[2] |

[1]Calculated in terms of pelargonidin ($\epsilon$ = 17800, $\lambda_{max}$ = 504.5 nm)
[2]Calculated in terms of cyanidin ($\epsilon$ = 34700, $\lambda_{max}$ = 547 nm)

Example 8

Preparation of Tetraploid *Lobularia maritima* by Performing Additional Breeding and Selection Methods and Analysis of Anthocyanin Levels Another method of the present invention is a tetraploid *Lobularia* plant having anthocyanin levels much higher than 17.6 mg/gram dry weight and having increased petal pigmentation concentration by performing additional breeding and selection using the methods of Examples 1 to 5 until selections with increased pigmentation concentration are obtained. Selections from these backcrosses follow the same procedures outlined in Examples 1 to 5 until inbred lines with increased pigmentation concentration are developed. Cytological analysis as outlined in Example 6 and anthocyanin analysis, as outlined in Example 7, is performed to quantify anthocyanin levels much higher than 17.6 mg/gram petal dry weight.

DEPOSIT INFORMATION

A deposit of the Ball Horticultural Company and proprietary tetraploid *Lobularia* seeds having flower petals that contain at least one anthocyanin disclosed above and recited in the appended claims has been made with the American Type Culture Collection (ATCC), 10801 University Boulevard, Manassas, Virginia 20110. The date of deposit was Mar. 18, 2008. The deposit of 2,500 seeds was taken from the same deposit maintained Ball Horticultural Company since prior to the filing date of this application. All restrictions will be removed upon granting of a patent, and the deposit is intended to meet all of the requirements of 37 C.F.R. §§1.801-1.809. The ATCC Accession Number is PTA-9082. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed:

1. A tetraploid *Lobularia maritima* plant having flower petals that contain at least one anthocyanin, wherein a sample of representative seed of a tetraploid *Lobularia maritima* plant having flower petals that contain at least one anthocyanin was deposited under ATCC Accession No. PTA-9082.

2. Pollen of the tetraploid *Lobularia maritima* plant of claim 1.

3. An ovule of the tetraploid *Lobularia maritima* plant of claim 1.

4. The tetraploid *Lobularia maritima* plant of claim 1, wherein said anthocyanin is the glycosylated derivative of cyanidin, pelargonidin or a combination thereof.

5. The tetraploid *Lobularia maritima* plant of claim 1, wherein said anthocyanin constitutes about 0.05 mg/g petal dry weight and wherein said anthocyanins are assayed as aglycons.

6. The tetraploid *Lobularia maritima* plant of claim 1, wherein said anthocyanin constitutes about 3 mg/g petal dry weight and wherein said anthocyanins are assayed as aglycons.

7. The tetraploid *Lobularia maritima* plant of claim 1, wherein said anthocyanin constitutes about 18.0 mg/g petal dry weight and wherein said anthocyanins are assayed as aglycons.

8. A *Lobularia maritima* plant, or a part thereof, produced by growing the seed of claim 1.

9. A tissue culture of produced from protoplasts or cells from the plant of claim 8, wherein said cells or protoplasts of the tissue culture are produced from a plant part selected from the group consisting of leaf, pollen, embryo, cotyledon, hypocotyl, meristematic cell, root, root tip, pistil, anther, flower, stem, ovule and petiole.

10. A *Lobularia maritima* plant regenerated from the tissue culture of claim 9.

11. A method of producing a hybrid tetraploid *Lobularia maritima*, the method comprising the steps of:
  a. Crossing a tetraploid *Lobularia maritima* plant with another tetraploid *Lobularia maritima* plant, wherein the tetraploid *Lobularia maritima* plant of claim 1 is either the female parent or the male parent, or both the female parent and the male parent,
  b. Recovering the resulting seed,
  c. Planting the resulting seed and growing said seed into plants, and
  d. Selecting a hybrid plant.

12. A hybrid tetraploid *Lobularia maritima* plant, or a part thereof, produced by the method of claim 11.

13. A method of producing a tetraploid *Lobularia maritima* inbred, the method comprising the steps of:
  a. Self- or sib-pollinating the tetraploid *Lobularia maritima* plant of claim 1, recovering the resulting seed, planting the resulting seed, growing said seed into plants, and selecting one or more progeny plants;
  b. Self- or sib-pollinating the selected progeny plant of step a, recovering the resulting seed, planting the resulting seed, growing said seed into plants, and selecting a plant; and
  c. Repeating step b three or more times in succession to produce selected fourth or higher progeny plants until an inbred is selected.

14. An inbred tetraploid *Lobularia maritima* plant, or a part thereof, produced by the method of claim 13.

15. A hybrid tetraploid *Lobularia maritima* plant, or a part thereof, produced by crossing the inbred tetraploid *Lobularia maritima* plant of claim 14 with another tetraploid *Lobularia maritima* plant.

* * * * *